United States Patent [19]

McAfee et al.

[11] Patent Number: 5,477,857
[45] Date of Patent: Dec. 26, 1995

[54] DIAGNOSTIC USES OF HYDRAZINOADENOSINES

[75] Inventors: Donald A. McAfee; Geoffrey Allan, both of Richmond; Richard J. Barrett, Midlothian, all of Va.

[73] Assignee: Discovery Therapeutics, Inc., Richmond, Va.

[21] Appl. No.: 119,774

[22] Filed: Sep. 10, 1993

[51] Int. Cl.⁶ ........................................................ A61B 6/00
[52] U.S. Cl. ............................ 128/654; 514/46; 514/261; 128/695 R; 128/630
[58] Field of Search ................................ 128/653.2, 653.4, 128/654, 659; 424/9; 514/46, 47; 600/1–4

[56] References Cited

U.S. PATENT DOCUMENTS

| | | | |
|---|---|---|---|
| 4,824,660 | 4/1989 | Angello et al. | 424/1.1 |
| 5,063,233 | 11/1991 | Chen et al. | 514/266 |
| 5,066,655 | 11/1991 | Olsson | 514/261 |
| 5,070,877 | 12/1991 | Mohiuddin et al. | 128/654 |
| 5,278,150 | 1/1994 | Olsson et al. | 514/46 |
| 5,284,834 | 2/1994 | Jacobsen et al. | 514/46 |
| 5,290,776 | 3/1994 | Caulkett et al. | 514/246 |
| 5,290,782 | 3/1994 | Suzuki et al. | 514/263 |

*Primary Examiner*—C. Fred Rosenbaum
*Assistant Examiner*—Chalin Smith
*Attorney, Agent, or Firm*—Sterne, Kessler, Goldstein & Fox

[57] ABSTRACT

The present invention discloses a method for measuring myocardial function in a mammal in need of such measurement by:

a) administering 0.01–15 µg/kg/min of a compound of the formula:

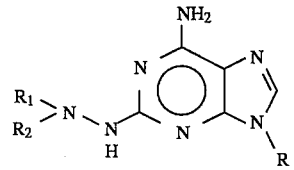

where $R_1$ is hydrogen or the group

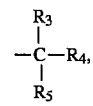

where $R_3$ and $R_4$ are the same or different and are hydrogen, $C_1$ to $C_{12}$ linear or branched alkyl, $C_3$ to $C_7$ cycloalkyl, $C_6$ to $C_{10}$ aryl unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_2$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a monosaccharide radical selected from the group consisting essentially of glucose, fructose, ribose, 2-deoxyribose, mannose, galactose, xylose and arabinose; and then:

b) performing a technique on said mammal to detect myocardial function.

This invention relates to the use of hydrazinoadenosines in the diagnosis of myocardial dysfunction by electrophysiologic analysis or by imaging the vasculature of the heart, especially under conditions that simulate stress.

4 Claims, No Drawings

DIAGNOSTIC USES OF HYDRAZINOADENOSINES

FIELD OF THE INVENTION

The present invention relates to the use of hydrazinoadenosines in the diagnosis of myocardial dysfunction by electrophysiologic analysis or by imaging the vasculature of the heart, especially under conditions that simulate stress.

BACKGROUND OF THE INVENTION

Adenosine has been known since the early 1920's to have potent vasodilator activity. It is a local hormone released from most tissues in the body during stress, especially hypoxic and ischemic stress (see Olsson et al., *Physiological Reviews*, 70(3), 761–845, 1990). As such, adenosine and adenosine-releasing agents are now commonly used to simulate the stress condition for diagnostic purposes (see *The Medical Letter*, 33(853), 1991).

Thallium-201 myocardial perfusion imaging is currently the most common approach in the use of stress-simulating agents as a means of imaging the coronary vessels to obtain a diagnosis of coronary artery disease. This is effected by injection of the stress agent such as adenesine at a dose of about 1 mg/kg body weight, followed by injection of the radionuclide, thallium-201, and scanning with a rotating gamma counter to image the heart and generate a scintigraph (see McNulty, *Cardiovascular Nursing*, 28(4), 24–29, 1992).

The mechanism underlying thallium-201 myocardial perfusion imaging is as follows: adenosine acting on coronary adenosine receptors causes relaxation of the coronary arterioles, thereby increasing blood flow throughout the heart. This effect is short-lasting and at a dose of 1 mg/kg, adenosine does not dilate other peripheral blood vessels to produce substantial systemic hypotension. Diseased or otherwise blocked coronary vessels will not further dilate in response to adenosine and the subsequent flow of thallium-201 through the heart will be less in these regions of hypoperfusion relative to other more normal areas of the heart. The resulting image allows the diagnostitian to quantitate the amount and severity of the coronary perfusion defect. This analysis is of paramount importance in selecting any further course of therapy and intervention by the physician [See U.S. Pat. Nos. 5,070,877 (Mohiuddin et al.) and 4,824,660 (Angello et al.)].

The use of adenosine and like-acting analogs is associated with certain side-effects. Adenosine acts on at least two subclasses of adenosine receptors, $A_1$ or $A_2$, both of which are found in the heart. The $A_1$ receptor subtype, when activated by adenosine, among other actions, slows the frequency and conduction velocity of the electrical activity that initiates the heart beat. Sometimes adenosine, particularly at doses near 1 mg/kg, even blocks (stops) the heart beat during this diagnostic procedure—a highly undesirable action. The $A_2$ receptor subtype is found in blood vessels and is further divided into $A_{2a}$ and $A_{2b}$ receptor subtypes (see Martin et al., *Journal of Pharmacology and Experimental Therapeutics*, 265(1), 248–253, 1993). It is the $A_{2a}$ receptor that is specifically responsible for mediating coronary vasodilation—the desired action of adenosine in the diagnostic procedure. Thus, the side-effects of adenosine and adenosine releasing agents result substantially from non-selective stimulation of the various adenosine receptor subtypes. Clearly, a better procedure would be to use a substance as a stress agent that selectively activates only the $A_{2a}$ receptor, is short acting and works at doses substantially below 1 mg/kg body weight.

Certain 2-hydrazinoadenosine derivatives are known to display superior selectivity as coronary vasodilators (see U.S. patent application Ser. No. 873,440; Niiya et al., *J. Med. Chem.*, 35, 4557–4561; and Ibid, 4562–4566, 1992). These substances are several thousand fold selective for the $A_{2a}$ adenosine receptor subtype. In addition to their selectivity, 2-hydrazinoadenosines are extremely potent. While this would seem an ideal combination for coronary dilation and diagnosis, the presence of $A_{2a}$ receptors on arterioles in other major vascular beds present a threat of severe systemic hypotension. It has now been discovered that these selective and potent derivatives of adenosine do not produce substantial systemic hypotension, are short acting, and appear to be more efficacious than adenosine in increasing coronary blood flow.

DESCRIPTION OF THE PREFERRED EMBODIMENTS

The method of the present invention uses the compounds of the following formula:

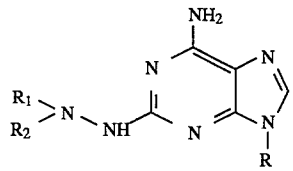

where $R_1$ is hydrogen or the group

where $R_3$ and $R_4$ are the same or different and are hydrogen, $C_1$ to $C_{12}$ linear or branched alkyl, $C_3$ to $C_7$ cycloalkyl, $C_6$ to $C_{10}$ aryl unsubstituted or substituted with $C_1$ to $C_6$ linear or branched alkyl, $C_1$ to $C_6$ linear or branched alkoxy, nitro, amino, amino substituted with at least one $C_1$ to $C_6$ linear or branched alkyl or phenyl, $C_2$ to $C_{10}$ aralkyl, $C_4$ to $C_8$ heteroaryl wherein said heteroatom is nitrogen, phosphorous, sulfur or oxygen, and $R_2$ is hydrogen, or taken together with $R_5$, forms a chemical bond, and R is a monosaccharide radical selected from the group consisting essentially of glucose, fructose, ribose, 2-deoxyribose, mannose, galactose, xylose and arabinose.

This invention utilizes the administration of the hydrazino compounds as a pharmacological stressor in conjunction with any one of several noninvasive diagnostic procedures available. For example, intravenous administration may be used in conjunction with thallium-201 myocardial perfusion imaging to assess the severity of myocardial ischemia. In this case, any one of several different radiopharmaceuticals may be substituted for thallium-201 (e.g., rubidium-82, technetium 99 m, derivatives of technetium 99 m, nitrogen-13, iodine 123, etc.). Similarly, the hydrazino compounds may be administered as a pharmacological stressor in conjunction with radionuclide angiography to assess the severity of myocardial dysfunction. In this case, radionuclide angiographic studies may be first pass or gated equilibrium studies of the right and/or left ventricle. Similarly, the compounds may be administered as a pharmacological stressor in conjunction with echocardiography to assess the presence of regional wall motion abnormalities. Similarly, the hydrazino compounds may be administered as a pharmacological stressor in conjunction with invasive measurements of coronary blood flow such as by intracardiac catheter to assess the functional significance of stenotic coronary vessels.

The above compounds provide a method for measuring myocardial function by infusing into a mammal in need of such infusion from about 0.001 to about 20 µg/kg/min of a compound of formula I. Preferably from about 0.01 to about 15 µg/kg/min is infused, most preferably from about 0.1 to about 10 µg/kg/min.

Various modes of administration are contemplated. These modes include administration in a parenteral dosage form, a sublingual or buccal dosage form, or administration by a transdermal device at a rate sufficient to cause vasodilation.

These compounds are used with diagnostic techniques to determine myocardial function. For example, the compounds are useful to image and analyze the vascular capacity of any tissue bed. These compounds can also be used in conjunction with any technique designed to image the heart for the purposes of determining coronary reserve capacity and detecting evidence of coronary heart disease. This method is also useful to replace adenosine or dipyridamole as pharmacological stressors in thallium-201 scintigraphic diagnosis of coronary function and heart disease. Further, these compounds are useful in imaging any vascular bed and, thus, the vascular function of any organ (eg. heart, brain, kidney, muscle, liver, fetus), in conjunction with any method capable of measuring function in that organ, such as scintigraphy, ultrasound, x-ray, laser, etc.

Typical of the imaging techniques used in practicing the method of the present invention are radiopharmaceutical myocardial perfusion imaging planar (conventional scintigraphy, single photon emission computed tomography (SPECT), position emission tomography (PET), nuclear magnetic resonance (NMR), perfusion contrast echocardiography, digital subtraction angiography (DSA) and ultrafast x-ray computed tomography (CINECT).

Typically, this invention is practiced by the intravenous infusion of vasodilatory doses (0.0001–10 µg/kg/min) over a short period, followed by the infusion of the imaging agent (e.g., thallium-201), followed by a procedure to detect, record and analyze the image (rotating gamma scintillation analyzer).

The preferred pharmacological stressor in practicing the present invention is selected from the group consisting of 2-alkylidenehydrazino adenosine derivatives. The most preferred agent is 2-cyclohexylmethylhydrazinoadenosine.

EXAMPLES

The method comprising the use of one or more of the hydrazoadenosines herein as a substitute for exercise in conjunction with imaging to detect the presence and/or assess the severity of ischemic ventricular dysfunction in humans wherein ischemic ventricular dysfunction is measured by any one of several imaging techniques including echocardiography, contrast ventriculography, or radionuclide angiography.

The method comprising the use of one or more of the hydrazoadenosines herein as a coronary hyperemic agent in conjunction with means for measuring coronary blood flow velocity to assess the vasodilatory capacity (reserve capacity) of coronary arteries in humans wherein coronary blood flow velocity is measured by any one of several techniques including Doppler flow catheter, digital subtraction angiography or other radiopharmaceutical imaging techniques.

The following Examples are to illustrate the invention, and are not intended to limit the invention.

TABLE 1

| AGON-IST EFFECT) | $A_{50}$ CORONARY ($A_{2a}$ EFFECT) | $A_{50}$ AORTA ($A_{2b}$ EFFECT) | $A_{50}$ EKG ($A_1$ EFFECT) | SELEC-TIVITY RATIO $A_1/A_{2a}$ |
|---|---|---|---|---|
| ADENO-SINE | 50 nM | 1,000 nM | 3,000 nM | 60 |
| Cmpnd A | 0.2 nM | 40,000 nM | 3,000 nM | 15,000 |

EXAMPLE 1

An isolated guinea pig heart preparation was set up using well-known techniques. The heart was perfused with a constant flow pump through the coronary vessels with a oxygenated balanced salt solution. The coronary perfusion pressure and the EKG were measured. Under constant flow, a decrease in coronary perfusion pressure indicates dilation ($A_{2a}$ effect). If the EKG shows decrease in heart rate or conduction velocity, this signals an $A_1$ effect. Various doses of adenosine and hydrazinoadenosines were given to the isolated heart, dose-response curves constructed, and the $A_{50}$ (concentration producing a 50% maximal response) calculated.

The data in Table 1 shows that 2-cyclohexylmethylhydrazinoadenosine (compound A) (see Niiya et al., *J. Med. Chem.*, 35, 4557–4561, 1992, Compound 9) is 250 times more potent than adenosine in causing coronary vasodilation. The $A_1/A_{2a}$ selectivity ratio for Compound A is much greater than that for adenosine and suggests that it would be superior to adenosine by avoiding side-effects such as heart block associated with activity at $A_1$ receptors.

EXAMPLE 2

A ring cut from the guinea pig aorta was placed in an organ bath and the tension developed by the ring was measured with a force-tension transducer. It is well known that relaxation of the precontracted aorta by adenosine analogs indicates an $A_{2b}$ effect.

When compared with the data from Example 1, Compound A is much more potent in relaxing coronary vessels than in relaxing the aorta (see Table 1). This coronary selectivity is greater than that for adenosine and suggests that Compound A is better suited than adenosine for selectively dilating coronary vessels. These data show the highest degree of potency and selectivity of the compounds of the current invention.

TABLE 2

| AGONIST | DOSE (µg/kg/min) | DURATION OF RESPONSE (min) | CHANGE IN SYSTOLIC BLOOD PRESSURE | CHANGE IN CIRCUMFLEX CORONARY FLOW |
|---|---|---|---|---|
| ADENO-SINE | 372 | 5 | −25% | +300% |
| COMPOUND A | 1 | 15 | −12% | +500% |

EXAMPLE 3

An anesthetized dog was prepared for cardiovascular function testing. Electromagnetic flow probes were placed on the circumflex coronary artery and the left anterior descending coronary artery. Systemic systolic and diastolic blood pressure and heart rate were also measured.

Adenosine (372 µg/kg/min) and Compound A (1.0 µg/kg/min) were separately infused and continuous measurements were made of the above cardiovascular parameters. The results in Table 2 were unexpected in that Compound A at 1/372 of the dose for adenosine was actually more effective than adenosine in increasing circumflex coronary blood flow (500% vs 300%), and produced less of the undesirable decrease in systolic blood pressure.

The duration of the systemic blood pressure response was only 15 minutes. This was an unexpected result since other $A_2$ selective agonists reported in the literature have much longer responses. For example, CGS 21680 produces a significant hypotensive response lasting more than 24 hrs. Furthermore, CGS 21680 produced significant reflex tachycardia—a potentially dangerous pharmacologic effect in patients with cardiomyopathies. (see Williams et al., "Adenosine Receptor Ligands as Therapeutic Entities: Molecular Specificity in Relation to Function and Therapeutic Activity", *Adenosine Receptors in the Nervous System*, J. A. Ribeiro, editor; Taylor and Francis, 1989, p. 61 and following).

EXAMPLE 4

Dogs were anesthetized and their circumflex coronary artery was stenosed to produce a cardiac perfusion deficit. One dog was infused with adenosine at 372 µg/kg/min for 6 minutes and then injected with thallium-201. A gamma scan produced a scintigram which clearly showed a perfusion defect. Similarly, another dog was infused with Compound A (0.6 µg/kg/min) before the thallium-201 scintigram was obtained. This dog too showed very clear evidence of a perfusion deficit proving that hydrazinoadenosines are suitable in this animal model of a routine clinical procedure.

Thus, compounds of the present invention produce greater vasodilation than maximal doses of adenosine, have a short duration of action and do not generate dangerous or undesirable hypotension or reflex tachycardia. The hydrazinoadenosines used in the method of the present invention are superior to adenosine for diagnostic procedures involving vasodilation in general and cardiac stress testing in particular.

What is claimed:

1. A method for measuring myocardial function in a mammal in need of such measurement comprising:
   (a) administering to said mammal from about 0.01 to about 15 µg/kg/min of 2-cyclohexylmethylhydrazinoadenosine as a pharmacological stressor thereby causing selective coronary vasodilation; and then
   (b) performing a technique on said mammal to measure myocardial function; such that myocardial function is measured while producing less systemic hypotension and reflex tachycardia compared to when adenosine is used as a pharmacological stressor.

2. The method of claim 1, wherein said 2-cyclohexylmethylhydrazinoadenosine is administered in a parenteral dosage form.

3. The method of claim 1 wherein said technique comprises administering an imaging agent to said mammal, and thereafter imaging said mammal.

4. The method of claim 1 wherein about 0.1 µg/kg/min to about 10 µg/kg/min of 2-cyclohexylmethylhydrazinoadenosine is administered to said mammal as a pharmacological stressor.

* * * * *